(12) United States Patent
Miller et al.

(10) Patent No.: US 8,753,834 B2
(45) Date of Patent: Jun. 17, 2014

(54) MICROBIAL DETECTION ARTICLE

(75) Inventors: Jesse D. Miller, Hudson, WI (US); Stephanie J. Moeller, Stillwater, MN (US); Kurt J. Halverson, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/519,284

(22) PCT Filed: Dec. 30, 2010

(86) PCT No.: PCT/US2010/062509
§ 371 (c)(1),
(2), (4) Date: Jun. 26, 2012

(87) PCT Pub. No.: WO2011/082305
PCT Pub. Date: Jul. 7, 2011

(65) Prior Publication Data
US 2012/0288888 A1    Nov. 15, 2012

Related U.S. Application Data

(60) Provisional application No. 61/291,245, filed on Dec. 30, 2009.

(51) Int. Cl.
*C12Q 1/04* (2006.01)
(52) U.S. Cl.
USPC .......................................................... 435/34

(58) Field of Classification Search
CPC . G01N 33/56911; G01N 33/569; C12Q 1/04; C12Q 1/06
USPC .......................................................... 435/34
See application file for complete search history.

(56) References Cited

U.S. PATENT DOCUMENTS

| | | |
|---|---|---|
| 4,279,995 A | 7/1981 | Woods et al. |
| 4,575,783 A | 3/1986 | Hammond |
| 4,868,110 A | 9/1989 | DesRosier et al. |
| 5,089,413 A | 2/1992 | Nelson et al. |
| 5,118,750 A | 6/1992 | Silver et al. |
| 5,194,374 A | 3/1993 | Rambach |
| 5,232,838 A | 8/1993 | Nelson et al. |
| 5,348,884 A | 9/1994 | Kulla |
| 5,364,766 A | 11/1994 | Mach et al. |
| 5,385,826 A | 1/1995 | Schell et al. |

(Continued)

FOREIGN PATENT DOCUMENTS

| | | |
|---|---|---|
| EP | 0 398 703 | 11/1990 |
| EP | 0 454 046 | 10/1991 |

(Continued)

OTHER PUBLICATIONS

US 4,476,226, 10/1984, Hansent et al. (withdrawn).

(Continued)

*Primary Examiner* — Karen Cochrane Carlson
*Assistant Examiner* — Jennifer M. H. Tichy

(57) ABSTRACT

The disclosure provides an article for the detection of a microorganism in a liquid sample. The article comprises a microporous membrane and a barrier layer to selectively regulate the contact between the sample and a detection reagent. A method of use is also provided.

13 Claims, 5 Drawing Sheets

(56) References Cited

U.S. PATENT DOCUMENTS

| | | | |
|---|---|---|---|
| 5,403,722 | A | 4/1995 | Floeder et al. |
| 5,434,056 | A | 7/1995 | Monget et al. |
| 5,443,963 | A | 8/1995 | Lund |
| 5,462,860 | A | 10/1995 | Mach |
| 5,601,998 | A | 2/1997 | Mach et al. |
| 5,629,170 | A | 5/1997 | Mondello |
| 5,635,367 | A | 6/1997 | Lund |
| 5,681,712 | A | 10/1997 | Nelson |
| 5,786,167 | A | 7/1998 | Tuompo et al. |
| 6,002,789 | A | 12/1999 | Olsztyn et al. |
| 6,022,682 | A | 2/2000 | Mach et al. |
| 6,251,624 | B1 | 6/2001 | Matsumura et al. |
| 6,331,429 | B1 | 12/2001 | Ushiyama |
| 6,368,817 | B1 | 4/2002 | Perry et al. |
| 6,565,749 | B1 | 5/2003 | Hou et al. |
| 6,596,532 | B1 | 7/2003 | Hyman et al. |
| 6,617,149 | B2 | 9/2003 | Restaino |
| 6,638,755 | B1 | 10/2003 | Mizuochi et al. |
| 7,150,977 | B2 | 12/2006 | Restaino |
| 7,298,885 | B2 | 11/2007 | Green et al. |
| 7,298,886 | B2 | 11/2007 | Plumb et al. |
| 7,351,548 | B2 | 4/2008 | Rambach |
| 2001/0041352 | A1 | 11/2001 | Reilly et al. |
| 2003/0088946 | A1 | 5/2003 | Ferguson et al. |
| 2003/0100104 | A1 | 5/2003 | Jeffrey et al. |
| 2004/0101954 | A1 | 5/2004 | Graessle et al. |
| 2004/0102903 | A1 | 5/2004 | Graessle et al. |
| 2005/0053266 | A1 | 3/2005 | Plumb et al. |
| 2006/0257967 | A1 | 11/2006 | Restaino |
| 2007/0259393 | A1 | 11/2007 | Restaino |
| 2008/0096195 | A1 | 4/2008 | Rambach |
| 2008/0176273 | A1* | 7/2008 | Eden et al. ...................... 435/30 |

FOREIGN PATENT DOCUMENTS

| | | |
|---|---|---|
| GB | 1 494 358 | 12/1977 |
| JP | 08-336381 | 12/1996 |
| JP | 2001-321196 | 11/2001 |
| JP | 2004-57054 | 2/2004 |
| JP | 2006-230219 | 9/2006 |
| WO | WO 82-02563 | 8/1982 |
| WO | WO 92-07899 | 5/1992 |
| WO | WO 96-06183 | 2/1996 |
| WO | WO 96-38533 | 12/1996 |
| WO | WO 98-06870 | 2/1998 |
| WO | WO 98-33069 | 7/1998 |
| WO | WO 99-18232 | 4/1999 |
| WO | WO 00-53721 | 9/2000 |
| WO | WO 01-14583 | 3/2001 |
| WO | WO 02-46354 | 6/2002 |
| WO | WO 2005-024047 | 3/2005 |
| WO | WO 2006-112709 | 10/2006 |
| WO | WO 2007-023186 | 3/2007 |
| WO | WO 2008-118400 | 10/2008 |
| WO | WO 2008-150779 | 12/2008 |
| WO | WO 2009-067498 | 5/2009 |
| WO | WO 2009-067503 | 5/2009 |
| WO | WO 2009-067513 | 5/2009 |
| WO | WO 2009-067518 | 5/2009 |
| WO | WO 2009-108229 | 9/2009 |
| WO | WO 2010-147918 | 12/2010 |
| WO | WO 2011-082305 | 7/2011 |
| WO | WO 2012/092181 | 7/2012 |

OTHER PUBLICATIONS

Baumgartner, A. et al."Quantitative Analysis of *E. coli* in Water Comparison of ECD Agar and Petrifilm™", Mitt. Gebiete Lebensm. Hyg.; vol. 84 1993, pp. 382-387.

Buhler, H.P. et al.; "Microbiological Evaluation of Drinking water: Modified Application of the 3M Petrifilm-Systems under Field Conditions", Schweiz Z. Milit. Med., vol. 70, No. 1, 1993; pp. 9-12.

Ingham, C.J. et al. "Growth and Multiplexed Analysis of Microorganisms on a Subdivided, Highly Porous, Inorganic Chip Manufactured from Anapore", Applied and Environmental Microbiology, vol. 71, No. 12, 2005; pp. 8978-8981.

Sadler, P.W. et al.; "Synthesis and Absorption Spectra of Symmetrical Chloroindigos". J. Am. Chem. Soc., vol. 78, 1956; pp. 1251-1255.

Sambrook, J. et al.; Molecular Cloning—A Laboratory Manual, Third Edition, vol. 2, Cold Spring Harbor Laboratory Press, Cold Spring Harbor, NY, (2001), Title, copyright and Table of Contents 18 pages.

Schraft, H. et al.; "Enumeration of heterotrophs, fecal coliforms and *Escherichia coli* in water: comparison of 3M™ Petrifilm™ plates with standard plating procedures", Journal of Microbiological Methods, vol. 60, 2005; pp. 335-342.

Food and Drug Administration Bacteriological Analytical Manual ("BAM"), 8$^{th}$ Ed., Revision A, (1998), AOAC International, Gaithersburg, MD, Title, copyright and Table of Contents 4 pages.

"Standard Methods for the Examination of Dairy Products", 17$^{th}$ Edition, Edited by H. M. Wehr et al.; The American Public Health Association, Washington, D.C., 2004, Title, copyright and Table of Contents 6 pages.

"Standard Methods for the Examination of Water and Wastewater," 20$^{th}$ Edition; Edited by L. S. Clesceri et al.; American Public Health Association; 1998, Title, copyright and Table of Contents 23 pages.

"AOAC Official Method 991.14 Coliform and *Escherichia coli* Counts in Foods—Dry Rehydratable Film (Petrifilm™ *E.coli*/Coliform Count Plate™ and Petrifilm™ Coliform Count Plate™) Methods", Official Methods of Analysis of AOAC International, 18$^{th}$ Edition, 2005, Current through Revision 4, 2011, AOAC International, Gaithersburg, MD, Title, copyright and method 3 pages.

ISO 9308-1. Water quality—Detection and enumeration of *Escherichia coli* and coliform bacteria—Part 1: Membrane filtration method, 2007, 24 pages.

Brochure entitled "3M Petrifilm™ Coliform Count Plate—Interpretation Guide"; #70-2008-4573-6 (1291.2) DPI; 1999; 6 pgs.

Donofrio et al. "Evaluation of Four Membrane Filter Materials for Use with 3M™ Petrifilm™ *E. coli* Coliform Count Plates to Enumerate *Escherichia coli* in Water Sample "; see www.foodprotection. org/files/annual_meeting/poster-abstracts-2009.pdf, p. 142 (2009).

\* cited by examiner

MICROBIAL DETECTION ARTICLE

CROSS REFERENCE TO RELATED APPLICATIONS

This application claims the benefit of U.S. Provisional Patent Application No. 61/291,245, filed Dec. 30, 2009, which is incorporated herein by reference in its entirety.

BACKGROUND

When surfaces become contaminated with bacteria, fungi, yeasts, viruses, or other microorganisms, or "microbes," sickness (morbidity) and, sometimes, death (mortality) may result. This is particularly true when surfaces in food processing plants and healthcare facilitates (e.g., hospitals) become contaminated with microorganisms.

In food processing plants, surfaces (e.g., solid surfaces, equipment surfaces, protective clothing, etc.) may become contaminated. Such contamination may be caused by or transferred to meat or other foods. In healthcare facilities, microbes may be released onto surfaces (e.g., solid surfaces, equipment surfaces, clothing, etc.) from infected individuals or otherwise. Once a surface becomes contaminated with microbes, contact with the contaminated surface may easily and readily transfer microbes to other locations, such as another surface, an individual, equipment, food, or the like.

As is well known, microbial contamination and transfer in certain environments may pose significant health risks. For example, the food that leaves a contaminated food processing plant will subsequently be eaten, and may cause sickness and, possibly, death. Microorganisms such as *Listeria monocytogenes, Salmonella enteriditis*, and *Escherichia coli* O157:H7 are of particular concern.

Microbial contamination is of concern in healthcare facilities since some of the patients of such facilities often suffer from infections by pathogenic microbes and, thus, bring the pathogenic microbes into such facilities. Further, many of those who are present in such facilities (e.g., patients) are sick and may be immunologically compromised. These individuals are, thus, at increased risk of becoming sick from infection by the contaminating microbes.

SUMMARY

The present disclosure relates to articles and methods that are used to detect a microorganism. In particular this disclosure relates to a multi-layer detection article that can be used to permit the growth of microorganisms for a limited period of time before repositioning or removing one of the layers to expose the microorganisms to a detection reagent.

In one aspect, the present disclosure provides an article for detecting or enumerating microorganisms in a sample. The article can comprise a base member, a microporous membrane, a cover sheet, and a barrier layer. The base member can comprise a self-supporting water impervious substrate with upper and lower major surfaces. The upper major surface of the base member can comprise a first dry coating that includes a cold water-soluble gelling agent. The cover sheet can comprise a second dry coating that includes a detection reagent. The barrier layer can be configured to form a fluid barrier between the microporous membrane and the cover sheet. The microporous membrane can be disposed between the base member and the barrier layer.

In any of the above embodiments, the article further can comprise a spacer. The spacer can comprise an aperture. The spacer can be coupled to the base member to form a sample-receiving well.

In any of the above embodiments, the cover sheet can be attached to the base member. In any of the above embodiments, the microporous membrane can be attached to the base member. In any of the above embodiments, the barrier layer can be attached to the base member. In any of the above embodiments, the barrier layer can be detachably attached to the base member.

In any of the above embodiments, the microporous membrane can comprise a material selected from the group consisting of polyethersulfone, nylon, polycarbonate, polyester, cellulose acetate, mixed cellulose esters, polyvinylidene fluoride, nitrocellulose, a ceramic, a derivative of any of the foregoing, and a combination of any two or more of the foregoing.

In any of the above embodiments, the microporous membrane further can comprise a permeation boundary. In any of the above embodiments, the article further can comprise a nutrient medium. In any of the above embodiments, the article further can comprise a selective agent. In any of the above embodiments, the article further can comprise a plurality of detection reagents. In any of the above embodiments, at least two of the plurality of detection reagents can differentiate at least two types of microorganisms.

In any one of the above embodiments, the cover sheet further can comprise a cold water-soluble gelling agent.

In another aspect, the present disclosure provides a method of detecting the presence or absence of a microorganism in a sample. The method can comprise providing a liquid sample suspected of containing a microorganism and a detection article. The detection article can comprise a base member, a microporous membrane, a cover sheet, and a barrier layer that forms a fluid barrier between the microporous membrane and the cover sheet. The base member can comprise a first dry coating that includes a cold water-soluble gelling agent. The cover sheet can comprise a second dry coating that includes a detection reagent. The microporous membrane can be disposed between the base member and the barrier layer. The method further can comprise contacting a predetermined amount of the sample with the first dry coating. The method further can comprise contacting the microporous membrane with the sample. The method further can comprise incubating the article for a first period of time. The method further can comprise repositioning the barrier layer to provide contact between the cover sheet and the microporous membrane. The method further can comprise incubating the article for a second period of time and observing an indication of the presence or absence of microbial growth.

In any of the above embodiments of the method, repositioning the barrier layer can comprise removing the barrier layer from the article.

In any of the above embodiments of the method, the article further can comprise a spacer that forms a sample-receiving well with the base member. In these embodiments, contacting a predetermined amount of the sample with the first dry coating can comprise transferring the sample into the sample-receiving well.

In any of the above embodiments of the method, the method further can comprise mixing the sample with a nutrient, a selective agent, a detection reagent, or a combination of any two or more of the foregoing.

In any of the above embodiments of the method, the first period of time can be about one hour to about 48 hours.

In any of the above embodiments of the method, the second period of time can be about fifteen minutes to about ninety-six hours.

In any of the above embodiments of the method, at least a portion of the first dry coating can comprise a plurality of detection reagents. In these embodiments, observing an indication of microbial growth can comprise detecting and differentiating two or more types of microorganisms.

In any of the above embodiments of the method, observing an indication of the presence or absence of microbial growth can comprise enumerating at least one type of microorganism. In any of the above embodiments of the method, observing an indication of the presence or absence of microbial growth can comprise obtaining an image of the article. In any of the above embodiments of the method, observing an indication of the presence or absence of microbial growth further can comprise printing, displaying, or analyzing the image.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a sample comprising "a" microorganism can be interpreted to mean that the sample can include "one or more" microorganisms.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The invention will be further explained with reference to the drawing figures listed below, where like structure is referenced by like numerals throughout the several views.

FIG. 1b is a top view of the detection article of FIG. 1a.

FIG. 1c is a top perspective view, partially in section, of the detection article of FIG. 1a.

FIG. 3b is a top view of the detection article of FIG. 3a.

FIG. 3c is a top perspective view, partially in section, of the detection article of FIG. 3a.

DETAILED DESCRIPTION

Figure 1A:
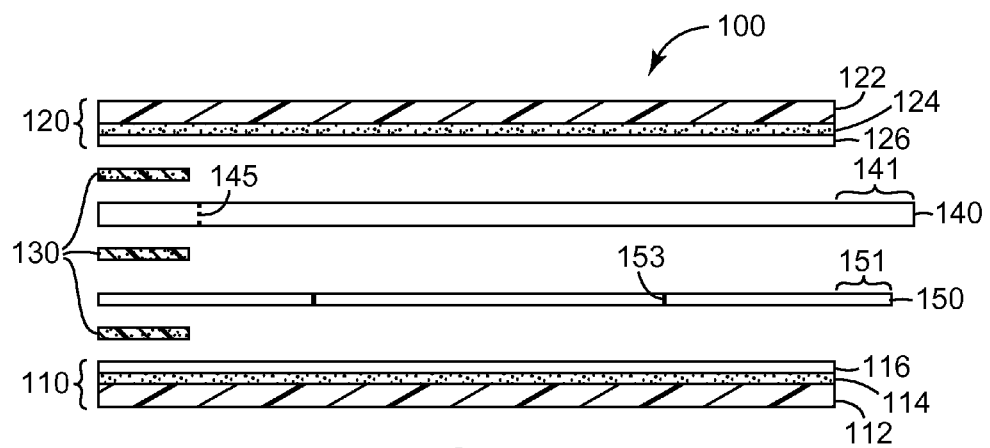
FIG. 1a is an exploded side view of one embodiment of a detection article comprising a microporous membrane according to the present disclosure.

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways. Also, it is to be understood that the phraseology and terminology used herein is for the purpose of description and should not be regarded as limiting. The use of "including," "comprising," "containing," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports and couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure is generally directed to methods and articles for detecting a microorganism in a liquid sample. The multi-layer detection articles provide i) a repositionable or removable barrier layer configured to control the exposure of a growing microorganism to a detection reagent and/or a selective agent and ii) a microporous membrane to prevent direct contact between microorganisms, and progeny thereof, present in the liquid sample and the barrier layer. Preventing direct contact between the microorganisms and the barrier layer obviates the possibility of spreading microorganisms within and/or removing microorganisms from the article when the barrier layer is repositioned or removed from the article.

The inventive multilayer articles of the present disclosure permit the use of relatively high concentrations of a detection reagent in order to reduce the amount of time needed to detect a microorganism. The presence of a barrier layer in the article prevents the exposure of microorganisms to the detection reagent (which may be present in an amount that could be inhibitory or toxic to the microorganisms) during a first incubation period. After the first incubation period, the barrier layer can be repositioned or removed, thereby exposing the microorganisms, if present, to the detection reagent. The articles of the present disclosure can comprise an optional lysis agent and/or selective agent that may also be sequestered by the barrier layer from contact with the microorganisms during the first incubation period.

The inventive articles and methods permit the use of diffusible detection reagents. When used in traditional articles (e.g., agar petri dishes), diffusible detection reagents (e.g., chromogenic or fluorogenic enzyme substrates, described below, that are hydrolyzed to a water-soluble, detectable product) can spread laterally through the detection device as large, colored or fluorescent zones. These zones may overlap two or more microorganism colonies, making it difficult to determine whether the zone was produce by only one or by more than one of the colonies. Providing an article that permits growth of microorganisms before they are exposed to the diffusible detection reagent, the user can reduce the amount of time that the microorganisms are exposed to the reagent, thereby minimizing the diffusion of the indicator and reducing the size of the corresponding colored or fluorescent zones. Thus, the inventive articles and methods improve the resolution of more than one microorganism colonies as compared to traditional articles and methods.

Unless otherwise defined, all technical and scientific terms used herein have the same meaning as commonly understood by one of ordinary skill in the art to which this invention belongs. Methods and materials similar or equivalent to those described herein can be used in the practice of the present invention, and exemplified suitable methods and materials are described below. For example, methods may be described which comprise more than two steps. In such methods, not all steps may be required to achieve a defined goal and the invention envisions the use of isolated steps to achieve these discrete goals. The disclosures of all publications, patent applications, patents and other references are incorporated herein by reference in their entirety. In addition, the materials, methods, and examples are illustrative only and not intended to be limiting.

"Target microorganism", as used herein, refers to a particular microorganism (i.e., a species of microorganism) or a particular group of microorganisms (e.g., a particular genus of microorganisms, coliform bacteria, antibiotic-resistant bacteria) to be detected.

Samples and Microorganisms

One aspect of the present invention is that it may be used to detect organisms present on a wide variety of surfaces. The devices and methods of the present invention may be used for a variety of applications where it is desirable to detect the presence or absence of microorganisms in a sample; including, but not limited to, food samples (e.g. raw materials, in-process food materials, finished products), surfaces (e.g., environmental surfaces, food processing surfaces, equipment), water (e.g., surface water, process water), and beverages (e.g., raw milk, pasteurized milk, juice). The samples may consist substantially of solid, semi-solid, gelatinous, or liquid material, alone or in various combinations. The devices of the invention, as well as the inventive methods, may be used to determine, qualitatively or quantitatively, the presence of one or more microorganisms of interest.

An exemplary clinical analyte of interest to detect is *Staphylococcus aureus* ("*S. aureus*"). This is a pathogen causing a wide spectrum of infections including: superficial lesions such as small skin abscesses and wound infections; systemic and life threatening conditions such as endocarditis, pneumonia and septicemia; as well as toxinoses such as food poisoning and toxic shock syndrome. Some strains (e.g., Methicillin-Resistant *S. aureus* or MRSA) are resistant to all but a few select antibiotics.

Exemplary analytes of interest to detect in food processing areas are members of the genus *Listeria*. *Listeria* are classified as gram-positive, rod-shaped bacteria and consist of the species *Listeria monocytogenes, L. innocua, L. welshimeri, L. seeligeri, L. ivanovii*, and *L. grayi*. Among these, *L. monocytogenes* is responsible for the majority of human listeriosis cases and immunocompromised, pregnant women, elderly, and newborns have increased susceptibility to infection. The most common symptoms of listeriosis are septicemia, meningitis, and miscarriages. Other microorganisms of particular interest for analytical purposes include prokaryotic and eukaryotic organisms, particularly Gram positive bacteria, Gram negative bacteria, fungi, mycoplasma, and yeast. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Vibrio* spp., *Clostridium* spp., *Corynebacteria* spp. as well as, *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis, Streptococcus pneumoniae, S. agalactiae, S. pyogenes, Enterococcus faecalis*, Vancomycin Resistant *Enterococcus* (VRE), Vancomycin Resistant *Staphylococcus aureus* (VRSA), Vancomycin Intermediate-resistant *Staphylococcus aureus* (VISA), *Bacillus anthracis, Pseudomonas aeruginosa, Escherichia coli, Aspergillus niger, A. fumigatus, A. clavatus, Fusarium solani, F. oxysporum, F. chlamydosporum, Vibrio cholera, V. parahemolyticus, Salmonella cholerasuis, S. typhi, S. typhimurium, Candida albicans, C. glabrata, C. krusei, Enterobacter sakazakii, Escherichia coli* O157, ESBL-containing microorganisms, and multiple drug resistant Gram negative rods (MDR).

Detection Articles

The present disclosure provides articles for detecting the presence or absence of a microorganism in a sample. FIG. 1*a* shows an exploded side view of one embodiment of a detection article 100 according to the present disclosure. The article comprises a base member 110 that includes a water impervious first substrate 112, an optional first adhesive layer 114 adhered to the first substrate 112, and a first dry coating 116.

The first substrate 112 preferably is self-supporting and does not substantially absorb water. Nonlimiting examples of suitable materials for the first substrate 112 include polyester, polypropylene, or polystyrene films. Other suitable materials include paper or cardboard materials that comprise a waterproof (e.g., polymeric) coating. The first substrate 112 may be transparent, translucent, or opaque, depending on whether one wishes to view bacterial colonies through the substrate 112. To facilitate the counting of bacterial colonies, the first substrate 112 may have a square grid pattern printed thereon as described in U.S. Pat. No. 4,565,783, which is incorporated herein by reference. The materials used to construct the first substrate 112 should be relatively inert to microorganisms and, preferably, should be compatible with a sterilization process (e.g., ethylene oxide sterilization).

In some embodiments, the base member 110 further may comprise an optional first adhesive layer 114 adhered to a major surface of the first substrate 112. First adhesive layer 114 may be water-insoluble, should be non-inhibitory to the growth of microorganisms, and should be capable of withstanding the sterilization process, if a sterilization process is used. Preferably, the first adhesive layer 114 is sufficiently transparent when wet to enable the viewing of bacterial colonies through the first substrate 112 coated with the adhesive layer 114. In some embodiments, the first adhesive layer 114 may comprise a pressure-sensitive adhesive such as a tackified high pressure sensitive iso-octyl acrylate/acrylic acid copolymer adhesive (96 wt. % iso-octyl acrylate and 4 wt. % acrylic acid), for example.

In some embodiments, the first substrate 112 may comprise a first adhesive layer 114 that covers an entire major surface of the substrate 112. In some embodiments, the first substrate 112 may comprise a first adhesive layer 114 that covers only a portion of a major surface of the substrate 112.

The first dry coating 116 comprises a cold water-soluble gelling agent (e.g., guar gum, xanthan gum, locust bean gum), as described in U.S. Pat. No. 4,565,783; which is incorporated herein by reference in its entirety. Optionally, the dry coating 116 may further comprise a nutrient medium, a selective agent, a detection reagent, or any combination of two or more of the foregoing. The nutrient medium, selective agent, and/or detection reagent should not substantially interfere with the gelling agent and generally will be chosen based upon the microorganisms to be detected. Nonlimiting examples of suitable nutrients, selective agents and detection reagents to detect microorganisms can be found in U.S. Pat. Nos. 4,565,783; 5,089,413; 5,443,963; 5,462,860; 5,601,998; 5,635,367; 5,681,712; and 5,364,766; each of which is incorporated herein by reference in its entirety. The amounts of nutrient medium, selective agent and/or detection reagent in the first dry coating 116 are prepared such that, when contacted with a predetermined amount of liquid sample, they facilitate the growth and/or detection of a microorganism.

In some embodiments, the first dry coating 116 (e.g., a dry powder gelling agent; optionally with a dry powdered nutrient, selective agent and/or detection reagent) may be coupled to the first substrate 112 by adhering the coating 116 the first adhesive layer 114, as described in U.S. Pat. No. 4,565,783, for example. In some embodiments, the first dry coating 116 may be coupled to the first substrate 112 by coating a liquid mixture comprising a gelling agent; optionally with a dry powdered nutrient, selective agent and/or detection reagent; onto the first substrate 112 or first adhesive layer 114 and subsequently drying the mixture, as described in U.S. Pat. No. 4,565,783, for example. In some embodiments, the first substrate 112 may comprise a first dry coating 116 that covers an entire major surface of the substrate 112. In some embodiments, the first substrate 112 may comprise a first dry coating 116 that covers only a portion of a major surface of the substrate 112.

Referring back to FIG. 1a, the article 100 further comprises a microporous membrane 150. In some embodiments, the microporous membrane 150, or a portion thereof, is coupled to the base member 110. In the illustrated embodiment, the microporous membrane 150 is coupled to the base member 110 via a strip of double-sided adhesive tape 130, although a person of ordinary skill in the art will recognize that other coupling means (e.g., adhesives, heat-bonding, ultrasonic welding) may be suitable. Optionally, the microporous membrane 150 may comprise a tab region 151 that extends beyond a peripheral boundary of the base member 110 and/or the cover sheet 120.

The microporous membrane 150 can comprise any one of a variety of water-permeable microporous membrane materials known in the art including, for example, cellulosic membranes (e.g., cellulose acetate, mixed cellulose esters, nitrocellulose), nylon, polycarbonate, polyethersulfone, nylon, polyester, polyvinylidene fluoride, ceramic, a derivative of any of the foregoing, and a combination of any two or more of the foregoing. The nominal pore size of the microporous membrane 150 is selected according to microorganisms to be detected. For example, a nominal pore size of about 0.05 μm to about 1.2 μm (e.g., 0.05 μm, 0.1 μm, 0.2 μm, 0.45 μm, 0.8 μm, or 1.2 μm), preferably about 0.2 μm to about 0.45 μm, can be used to detect bacteria. In some embodiments, a nominal pore size of about 0.05 μm to about 3 μm (e.g., 0.45 μm, 0.8 μm, 1.2 μm, or 3 μm), preferably about 0.45 μm to about 1.2 μm, can be used to detect yeast and/or molds.

In any embodiment, the microporous membrane 150 should be configured to form a barrier to prevent the transfer of microorganisms in a liquid sample deposited on the base member 110 from contacting the barrier layer 140. In some embodiments, this can be accomplished by selecting the sample volume and/or dimensioning the microporous membrane 150 such that the liquid sample cannot spread to or beyond the outer margin of the microporous membrane 150. In some embodiments (as shown in FIG. 1), the microporous membrane 150 can be dimensioned to be at least coextensive with the dimensions of the base member 110. Coupling the microporous membrane 150 to the base member 110, as described above, advantageously can keep the membrane 150 properly positioned to avoid direct contact between the sample and the barrier layer 140.

The microporous membrane 150 can further comprise an optional lateral permeation boundary 153 to confine the lateral permeation of liquid to a selected portion of the microporous membrane 150. The permeation boundary 153 comprises an area of the microporous membrane 150 that has been treated (e.g., a composition has been applied), for example, to restrict the movement of an aqueous sample across and/or through the microporous membrane. For example, a hydrophobic composition (e.g., wax) can be applied in a circular pattern (see FIG. 1b), for example, and allowed to penetrate the microporous membrane 150. The composition may form a barrier that substantially prevents the lateral diffusion of an aqueous liquid through the microporous membrane 150. Thus, a liquid sample in contact with the microporous membrane 150 in a region on one side of the permeation boundary 153 will be substantially prevented from spreading laterally through the microporous membrane 150 to the region on the other side of the permeation boundary.

The article 100 further comprises a barrier layer 140. In some embodiments, the barrier layer 140 is detachably coupled to the microporous membrane 150, as shown in FIG. 1. The barrier layer 140 may be coupled to the microporous membrane 150 via a strip of double-sided adhesive tape 130. Preferably the barrier layer 140 further comprises a detachment means (e.g., perforation 145) to facilitate the detachment and removal of the barrier layer 140 from the article 100. Optionally, the barrier layer 140 may comprise a tab region 141 that extends beyond a peripheral boundary of the base member 110 and/or the cover sheet 120.

It is recognized that other coupling means (e.g., adhesives, heat-bonding, ultrasonic welding) may be suitable to attach the barrier layer 140 to the microporous membrane 150. It is also recognized that the barrier layer 140 may be coupled directly to the base member 110, provided that the microporous membrane is disposed between the base member 110 and the barrier layer 140. In an alternative embodiment, certain low-adhesion adhesive mixtures, such as those described in U.S. Pat. No. 5,118,750; incorporated herein by reference in its entirety; may be used on at least one side of the double-sided adhesive tape 130 to form detachable attachments between the barrier layer and both the microporous membrane 150 and the cover sheet 120. In yet another alternative embodiment (not shown), the barrier layer 140 may be loosely disposed between the microporous membrane 150 and the cover sheet 120 before and/or after inoculating the article 100.

The barrier layer 140 should be water-resistant. The barrier layer 140 is preferably transparent to permit the observation of objects located beneath the barrier layer 140 and is substantially impermeable to bacteria, water and water vapor. Generally, the barrier layer 140 can have the same properties as base member 110. Exemplary materials for barrier layer 140 include, for example, polypropylene film (e.g., 1.6 mil biaxially-oriented polypropylene (BOPP)) or polyethylene film. The barrier layer 140 is shown with an optional extension (tab 141), which facilitates grasping and removing the barrier layer 140 from the article 110.

The article 100 further comprises a cover sheet 120. The cover sheet 120 preferably is coupled (either directly or indirectly) to the base member 110. In the illustrated embodiment, the cover sheet 120 is coupled to the barrier layer 140 via a strip of double-sided adhesive tape 130. It is recognized that other coupling means (e.g., adhesives, heat-bonding, ultrasonic welding) may be suitable to attach the cover sheet 120 to the microporous membrane barrier layer 140. It is also recognized that the cover sheet 120 may be coupled directly to the base member 110, provided that the microporous membrane is disposed between the base member 110 and the cover sheet 120. The cover sheet 120 includes a water-impervious second substrate 122, an optional second adhesive layer 124, and a second dry coating 126. The second dry coating 126 comprises a detection reagent to detect a microorganism.

The detection reagent may be detected visually and/or by using an automated detector. The automated detector may comprise an imaging system. The detection reagent may be chromogenic, fluorogenic, or luminogenic. In any embodiment, the detection reagent, when contacted with a predetermined amount of liquid sample reaches a concentration sufficient to detect a target microorganism. Advantageously, the amount of the detection reagent in the second dry coating 126 can be sufficiently high to rapidly detect the presence of a target microorganism even though the high concentration of detection reagent in the liquid sample also inhibits the growth of the target microorganism. In some embodiments, the amount of detection reagent in the second dry coating 126 is sufficient to detect a target microorganism even though it substantially inhibits the growth of the target microorganism. A relatively higher amount of detection reagent in the second dry 126 coating permits more rapid detection of the target microorganisms than a relatively lower amount of detection reagent even though the relatively higher amount may substantially inhibit growth of the microorganisms.

The detection reagent can be a nonspecific indicator of the type of microorganism present or it can be a specific indicator of the type of microorganism present. Nonlimiting examples of nonspecific detection reagents include pH indicators (e.g., azobenzene pH indicators (e.g., methyl red), sulfonphthalein pH indicators (e.g., bromocresol purple, chlorophenol red, bromthymol blue, bromcresol blue), and anthroquinone pH indicators (e.g., alizarin red s monohydrate 3,4-dihydroxy-9, 10-dioxo-2-anthracensulfonic acid, sodium salt)) and redox indicators (e.g., triphenyltetrazolium chloride (TTC), 3-[4,5-dimethylthiazol-2-yl]-2,5-diphenyltetrazolium bromide (MTT), 2,3-bis[2-methoxy-4-nitro-5-sulfophenyl]-2H-tetrazolium-5-carboxanilide inner salt (XTT), Nitro Blue Tetrazolium).

The detection reagent can be a specific indicator of the type of microorganism present. Specific detection reagents include, for example, substrates for enzymes (e.g., glycosidases, proteases, aminopeptidases, phosphatases, esterases, and the like) that are associated with certain microorganisms or groups of microorganisms.

The detection reagent may be capable of forming a colored precipitate. A variety of dyes are known that could be incorporated into the methods and devices of the present disclosure, including indolyl-containing dyes including, but not limited to, 5-bromo-4-chloroindolyl phosphate or disodium salts of that compound, 5-bromo-4-chloroindolyl pyranoside or disodium salts of that compound, including 5-bromo-4-chloro-3 indolyl-β-D-glucuronic acid, 5-bromo-4-chloro-3-indoxyl-β-D-galactoside, 5-bromo-4-chloro-3-indolyl-β-D-glucopyranoside, 6-chloro-3-indolylphosphate, 5-bromo-6-chloro-3-indolylphosphate.

Preferably, the colored precipitate is blue. Substrates that create a blue colored precipitate include, but are not limited to, 5-bromo-4-chloro-3-indoxyl-N-acetyl-β-D-galactosaminide, 5-bromo-4-chloro-3-indoxyl-N-acetyl-β-D-glucosaminide, 5-bromo-4-chloro-3-indoxyl-β-D-cellobioside, 5-bromo-4-chloro-3-β-D-fucopyranoside, 5-bromo-4-chloro-3-indoxyl-α-D-galactopyranoside, 5-bromo-4-chloro-3-indoxyl-β-galactopyranoside, 5-bromo-4-chloro-3-indoxyl-α-D-glucopyranoside, 5-bromo-4-chloro-3-indoxyl-β-D-glucopyranoside, 5-bromo-4-chloro-3-indoxyl-β-D-glucuronic acid, cyclohexylammonium salt, 5-bromo-4-chloro-3-indoxyl-β-D-glucuronic acid, sodium salt, and 5-bromo-4-chloro-3-indoxyl-β-D-xylopyranoside.

The dyes can serve as substrates for particular enzymes present within certain types of bacteria. For example, blue-precipitate producing dyes that are substrates for esterases include, but are not limited to, 5-bromo-4-chloro-3-indoxyl butyrate, 5-bromo-4-chloro-3-indoxyl caprylate, and 5-bromo-4-chloro-3-indoxyl palmitate. Substrates for phosphatases include, but are not limited to, 5-bromo-4-chloro-3-indoxyl phosphate di(2-amino-2-methyl-1,3-propanediol) salt, 5-bromo-4-chloro-3-indoxyl phosphate disodium salt, 5-bromo-4-chloro-3-indoxyl phosphate and p-toluidine salt, 5-bromo-4-chloro-3-indoxyl phosphate and the potassium salt.

Chromogenic dyes that are substrates for glycosidases include, but are not limited to, 3-indoxyl-β-D-galactopyranoside, 3-indoxyl-β-D-glucopyranoside, 3-indoxyl-β-D-glucuronic acid cyclohexylammonium salt, and 3-indoxyl-β-D-glucuronic acid sodium salt. Other chromogenic substrates for phophatases include, but are not limited to, 3-indoxyl phosphate di(2-amino-2-methyl-1,3-propanediol) salt, and 3-indoxyl phosphate disodium salt, 3-indoxyl phosphate p-toluidine salt. Substrates for sulfatases include, but are not limited to, 3-indoxyl sulfate potassium salt.

Precipitable dyes that produce a magenta color for glycosidases, esterases, phosphatases and sulfatases include, but are not limited to 5-bromo-6-chloro-3-indoxyl-N-acetyl-β-D-glucosaminide, 5-bromo-6-chloro-3-indoxyl-β-D-galactopyranoside, 5-bromo-6-chloro-3-indoxyl-β-D-galactopyranoside, 5-bromo-6-chloro-3-indoxyl-β-D-glucopyranoside, and 5-bromo-6-chloro-3-indoxyl-β-D-glucuronic acid, cyclohexylammonium salt as substrates for glycosidases; 5-bromo-6-chloro-3-indoxyl butyrate, 5-bromo-6-chloro-3-indoxyl caprylate, and 5-bromo-6-chloro-3-indoxyl palmitate serve as substrates for esterases; 5-bromo-6-chloro-3-indoxyl phosphate, p-toluidine salt for phosphatases and 5-bromo-6-chloro-3-indoxyl sulfate, potassium salt serve as substrates for sulfatases.

Precipitable dyes that produce a salmon color for glycosidases, esterases and phosphatases include, but are not limited to, 6-chloro-3-indoxyl-β-galactopyranoside, 6-chloro-3-indoxyl-β-D-glucopyranoside, and 6-chloro-3-indoxyl-β-D-glucuronic acid, cyclohexylammonium salt for glycosidases; 6-chloro-3-indoxyl butyrate, 6-chloro-3-indoxyl caprylate, and 6-chloro-3-indoxyl palmitate for esterases; and, 6-chloro-3-indoxyl phosphate, p-toluidine salt for phosphatases.

Chromogenic substrates that produce a purple color include 5-iodo-3-indoxyl-β-D-galactopyranoside and chromogenic substrates that produce a green color include N-methyl-indoxyl-β-D-galactopyranoside.

Other precipitable dyes include 4,6-dichloro-N-acetylindol-3-ol, 6-chloroindolyl-β-D-galactoside pentaacetate, 6-chloroindolyl-β-D-galactoside, 6-chloroindoxy-1,3-diacetate, 5-chloro-2-carboxyphenylglycine sodium salt, 4-chloroanthranilic acid, methyl[6-chloro-N-acetylindol-3-yl-(2,3,4-tri-O-acetyl-β-D-glucopyran oside)]uronate, 6-chloroindolyl-β-D-glucopyranoside uronate monocyclohexylammonium salt, chloroindigos reported by Sadler et al., J. Am. Chem. Soc. 78:1251-1255, 1956, as well as 4,6-dichloroindolyl-β-D-glucuronide, 6,7-dichloroindolyl-β-D-glucuronide, 6,7-dichloroindolyl-β-D-glucuronide, 4,6,7-trichloroindolyl-β-D-glucuronide, 4,6-dichloroindolyl-β-D-galactoside, 6,7-dichloroindolyl-β-D-galactoside, and 4,6,7-trichloroindolyl-β-D-galactoside.

Suitable detection reagents further include non-precipitating indicator dyes (i.e., water-soluble dyes that are capable of diffusing in a hydrogel). Non-precipitating indicator dyes include pH indicators (e.g., azobenzene pH indicators, sulfonphthalein pH indicators, and anthroquinone pH indicators, as described herein. Non-precipitating indicator dyes also include chromogenic enzyme substrates that react with an enzyme to release a water-soluble dye (e.g., p-nitrophenyl phosphate or p-nitrophenyl-β-D-glucoside, which each can be hydrolyzed to p-nitrophenol), and fluorogenic enzyme substrates, which can react with an enzyme to release a water-soluble fluorescent dye (e.g. 4-methylumbelliferyl phosphate or 4-methylumbelliferyl-β-D-glucoside, which each can be hydrolyzed to p-nitrophenol).

A problem with using non-precipitating dyes in traditional articles and methods (e.g., agar petri dish methods) is that the indicator dyes are typically incorporated into the agar and the microorganisms are able to react with the dyes during the entire growth period. This relatively lengthy period of exposure to the indicator dyes permits significant lateral diffusion of the water-soluble products which can result in large zones of indicator dye that overlap two or more colonies. Thus, in the traditional methods, the operator may not be able to distinguish which colony or colonies reacted with the indicator dye.

In contrast, methods of the present disclosure (described below) include a first incubation period during which the microorganisms, if present are not able to react with the detection reagent. Methods of the present disclosure further include a second incubation period in which the microorganisms, if present, are exposed to the detection reagent. Because the second incubation period can be relatively short (e.g., about 15 minutes, about 30 minutes, about 1 hour, about 2 hours, about 3 hours, about 4 hours, about 6 hours, about 8 hours, or about 10 hours), nonprecpitating indicator dyes do not have enough time to substantially diffuse through the gel formed from the liquid sample and the cold water soluble gelling agent. Advantageously, this permits the use of water-soluble indicator reagents that would diffuse too far from the vicinity of a colony if the indicator reagent was incubated for longer periods of time (e.g., 18 hours, 24 hours, 36 hours, or 48 hours, for example) with the microorganisms in a hydrogel.

The second substrate 122 preferably is transparent or translucent, to permit viewing or imaging of bacterial colonies through the substrate 122, and does not substantially absorb water. Nonlimiting examples of suitable materials for the second substrate 122 include polyester, polypropylene, or polystyrene films. Other suitable materials include paper or cardboard materials that comprise a waterproof (e.g., polymeric) coating. The materials used to construct the second substrate 122 should be relatively inert to microorganisms and, preferably, should be compatible with a sterilization process (e.g., ethylene oxide sterilization).

In some embodiments, the cover sheet 120 further may comprise an optional second adhesive layer 124 adhered to the second substrate 122. Second adhesive layer 124 may be water-insoluble, should be non-inhibitory to the growth of microorganisms, and should be capable of withstanding the sterilization process, if a sterilization process is used. Preferably, the second adhesive layer 124 is sufficiently transparent when wet to enable the viewing or imaging of bacterial colonies through the cover sheet 110. In some embodiments, the second adhesive layer 124 may comprise a pressure-sensitive adhesive such as a tackified high pressure sensitive iso-octyl acrylate/acrylic acid copolymer adhesive (96 wt. % iso-octyl acrylate and 4 wt. % acrylic acid), for example.

The second dry coating 126 comprises a detection reagent. Optionally, the second dry coating 126 may further comprise a cold water-soluble gelling agent (e.g., guar gum, xanthan gum, locust bean gum), as described in U.S. Pat. No. 4,565,783; a nutrient, a lysis agent, a selective agent, or any combination of two or more of the foregoing. The nutrient, selective agent, and/or lysis agent generally will be chosen based upon the microorganisms to be detected. Nonlimiting examples of suitable nutrients, selective agents and detection reagents to detect microorganisms can be found in U.S. Pat. Nos. 4,565,783; 5,089,413; 5,443,963; 5,462,860; 5,601,998; 5,635,367; 5,681,712; and 5,364,766; each of which is incorporated herein by reference in its entirety.

The optional lysis agent can partially or completely lyse a microorganism, allowing for the detection of an internal component (e.g., an enzyme) of the microorganism. Lysis agents include detergents, enzymes (e.g., lysozyme, lysostaphin) and bacteriophage.

In some embodiments, the second dry coating 126 may be coupled to the second substrate 122 by adhering the coating 126 to the second adhesive layer 124, as described in U.S. Pat. No. 4,565,783, for example. In some embodiments, the second dry coating 126 may be coupled to the second substrate 122 by coating a liquid mixture comprising a detection reagent; optionally with a gelling agent (e.g., a cold water soluble gelling agent), a nutrient, a selective agent and/or a lysis reagent; onto the second substrate 122 or second adhesive layer 124 and subsequently drying the mixture, as described in U.S. Pat. No. 4,565,783, for example.

The second dry coating 126 may include a detection reagent that, when contacted with a predetermined amount of liquid sample reaches a concentration sufficient to detect a target microorganism yet also inhibit the growth of the target microorganism. In some embodiments, the amount of detection reagent in the second dry coating 126 is sufficient to detect a target microorganism yet also substantially inhibit the growth of the target microorganism.

Figure 1B:
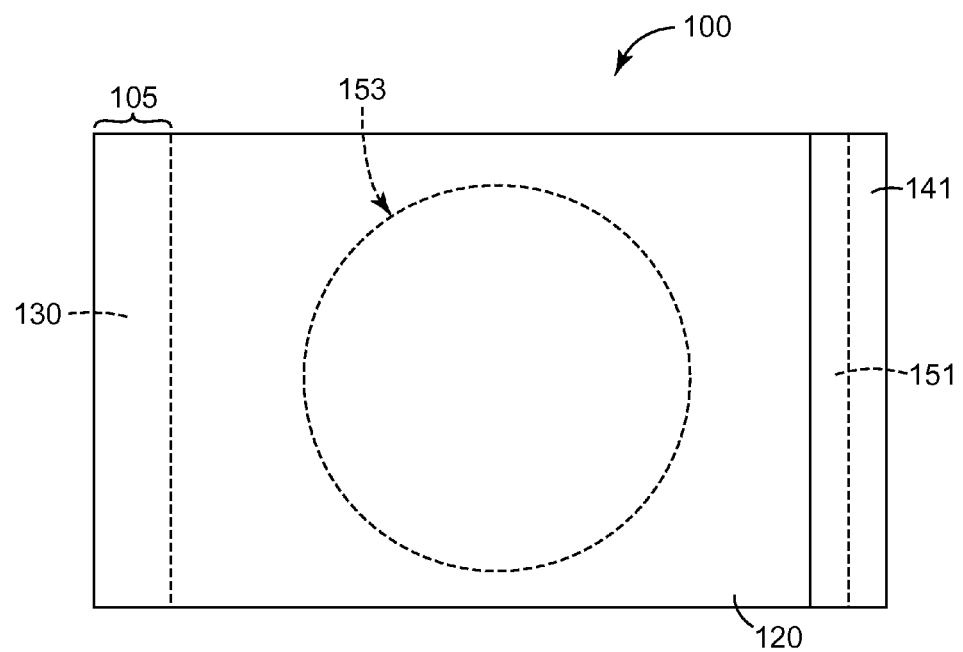

FIG. 1b shows a top view of the detection article 100 of FIG. 1a. The figure shows the cover sheet 120, the tab region 141 of the barrier layer, and the tab region 151 of the microporous membrane. The figure also shows the optional permeation boundary 153 and a hinge region 105 formed by the double-sided adhesive tape 130 aligned along an edge of the article 100.

Figure 1C:
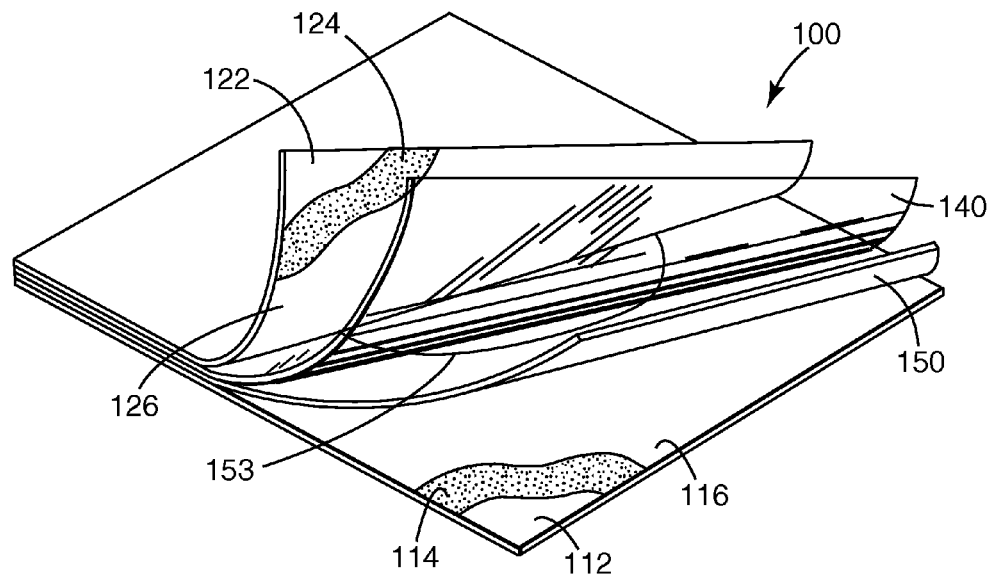

FIG. 1c shows a top perspective view of the article 100 of FIG. 1a. The article 100 comprises a base member 110 that includes a first substrate 112, optional first adhesive layer 114, and first dry coating 116. Also shown in FIG. 1c are the microporous membrane 150, the barrier layer 140, and the cover sheet 120 that includes a second substrate 122, an optional second adhesive layer 124, and a second dry coating 126. The microporous membrane 150 includes a permeation boundary 153, as described above.

Figure 2:
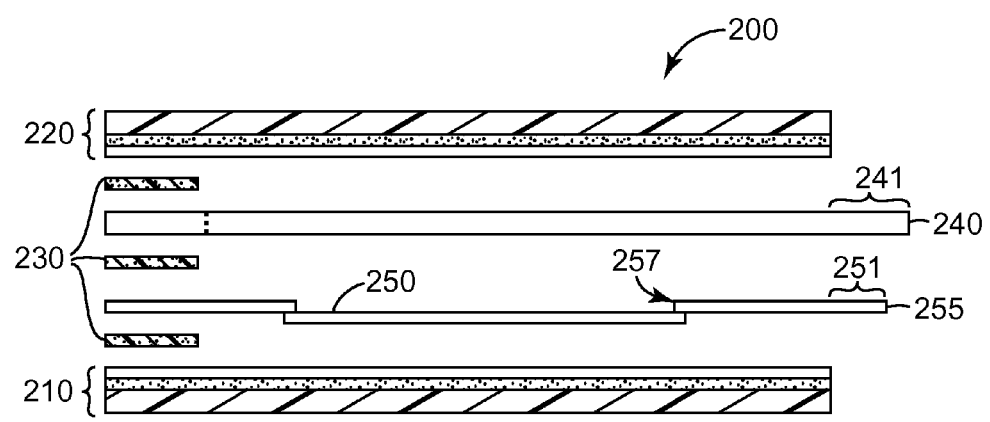
FIG. 2 is an exploded side view of one embodiment of a detection article comprising a microporous membrane coupled to a membrane carrier according to the present disclosure.

FIG. 2 shows an exploded side view of another embodiment of a detection article 200 according to the present disclosure. The article 200 comprises a base member 210, barrier layer 240, and cover sheet 220, as described above. The article 200 further comprises a membrane carrier 255 that includes a microporous membrane 250.

The membrane carrier 255 is disposed between the base member 210 and the barrier layer 240. In some embodiments, the membrane carrier 255 is coupled to the base member 210 and/or barrier layer 240 (e.g., via double-sided adhesive tape 230). The membrane carrier 250 may be coupled to the base member 210 and/or barrier layer 240 by alternative means, as described above.

The membrane carrier 255 is configured to support a microporous membrane 250. The membrane carrier 255 preferably is self-supporting and does not substantially absorb water. Nonlimiting examples of suitable materials for the membrane carrier 255 include polyester, polypropylene, or polystyrene films. Other suitable materials include paper or cardboard materials that comprise a waterproof (e.g., polymeric) coating. The membrane carrier 255 may be transparent, translucent, or opaque. The membrane carrier 255 further comprises an aperture 257 that permits fluid communication from the base member 210 through the microporous membrane 250 to the cover sheet 220, when the barrier layer 240 is detached from the article 200. Optionally, the membrane carrier 255 may comprise a tab region 251 that extends beyond a peripheral boundary of the base member 210 and/or the cover sheet 220.

The aperture 257 can be any shape, such as a circle, a square, a rectangle, a hexagon, an octagon, an oval, or an irregular shape, for example.

The microporous membrane 250 can be dimensioned to be coextensive with the aperture 257. In some embodiments, the microporous membrane 250 is smaller than the aperture 257. In some embodiments, the microporous membrane 250 is larger than the aperture 257, as shown in FIG. 2. The microporous membrane can be dimensioned to provide an area suitable to distribute a predetermined amount of liquid sample. For example, to distribute a 1 milliliter sample, the microporous membrane 250 can be about 20 $cm^2$ to about 30 $cm^2$. For example, to distribute a 5 milliliter sample, the microporous membrane 250 can be about 45 $cm^2$.

The microporous membrane 250 is coupled to the membrane carrier 255 (preferably, by an adhesive) such that the coupling prevents the passage of liquid sample between the membrane carrier 255 and the microporous membrane 250. Thus, the passage of liquid from one major surface of the microporous membrane 250 to the other major surface substantially requires the passage of the liquid through the membrane 250.

Figure 3A:
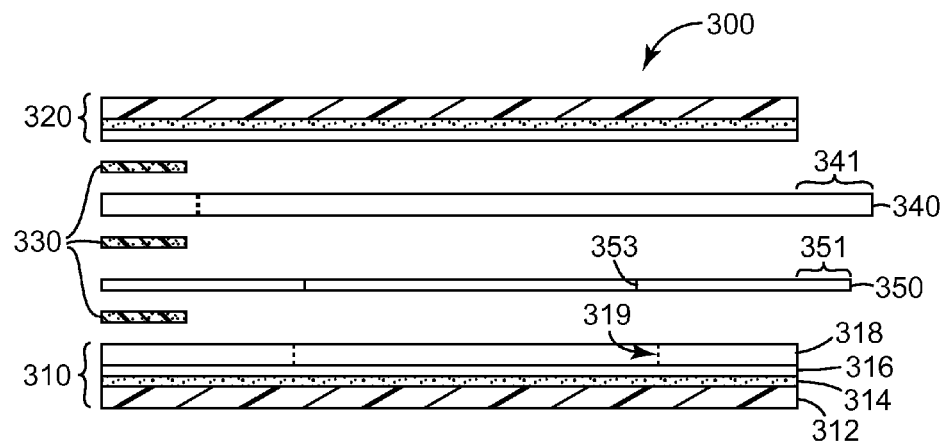
FIG. 3a is an exploded side view of one embodiment of a detection article comprising a spacer and a microporous membrane according to the present disclosure.

FIG. 3a shows an exploded side view of another embodiment of a detection article 300 according to the present disclosure. The article 300 comprises a cover sheet 320, a barrier layer, and a microporous membrane 350, as described herein. The barrier layer 340 and microporous membrane 350 further comprise optional tab regions 341 and 351, respectively, as described herein. The microporous membrane 350 further comprises optional permeation barrier 353, as described herein.

In this embodiment, the base member 310 comprises a substrate 312, optional adhesive layer 314, and dry coating 316, as described herein. The base member further comprises a spacer 318. The spacer 318, which comprises an aperture 319, should be constructed from a water-insoluble material. The walls of the aperture 319, together with the base member 310 form a sample-receiving well of predetermined size and shape to confine a volume of liquid sample deposited in the article 300. The spacer 318 should be thick enough and the aperture 319 large enough to form a well of the desired volume, e.g., 1 milliliter, 2 milliliters, 3 milliliters, 5 milliliters, or more. Closed cell polyethylene foam or polystyrene foam are suitable materials for the spacer 318, but any material which is hydrophobic (non-wetting), inert to microorganisms, and, preferably, capable of withstanding a sterilization process may be used. The spacer 318 can be coupled to the base member 310, for example, by an adhesive, as described in U.S. Pat. No. 4,565,783.

In some embodiments, the microporous membrane 350 can be configured in the article 300 with a permeation boundary 353 that coincides with the shape, size, and position of the aperture 319. In some embodiments, the area of the microporous membrane 350 bounded by the permeation boundary 353 may be larger than the area of the aperture 319. In these embodiments, the permeation boundary 353 can prevent sample liquid from excessively diffusing within the microporous membrane 350.

The microporous membrane 350 should be positioned such that, during use, at least of portion of the microporous membrane 350 overlays the aperture 319. Preferably, during use, the microporous membrane 350 is positioned such that the microporous membrane 350 substantially overlays the aperture 319. In some embodiments, the area of the microporous membrane 350 is larger than the area of the aperture 319 and the microporous membrane 350 extends beyond the perimeter of the aperture 319.

In some embodiments, the base member 310, microporous membrane 350, barrier layer 340, and cover sheet 320 may be coupled to each other, as shown in FIG. 3a. They may be coupled to each other, for example, with individual segments of double-sided adhesive tape 330. However, other coupling means, described above, may be suitable.

Figure 3B:
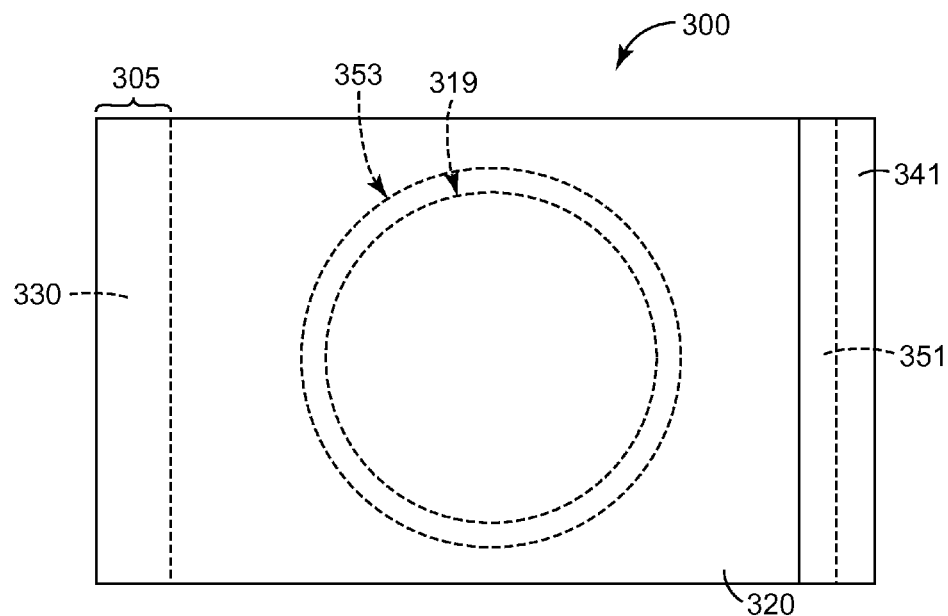

FIG. 3b shows a top view of the detection article 300 of FIG. 3a. The figure shows the cover sheet 320 the tab region 341 of the barrier layer, and the tab region 351 of the microporous membrane. FIG. 3b also shows the optional permeation boundary 353, the aperture 319, and a hinge region 305 formed by the double-sided adhesive tape 330 aligned along an edge of the article 300. Although the aperture 319 of FIG. 3b is circular in shape, apertures 319 with other shapes may be suitable. For example, the aperture 319 may be in the shape of a square, an oval, a rectangle, a hexagon, an octagon, or it may be an irregular shape.

Figure 3C:
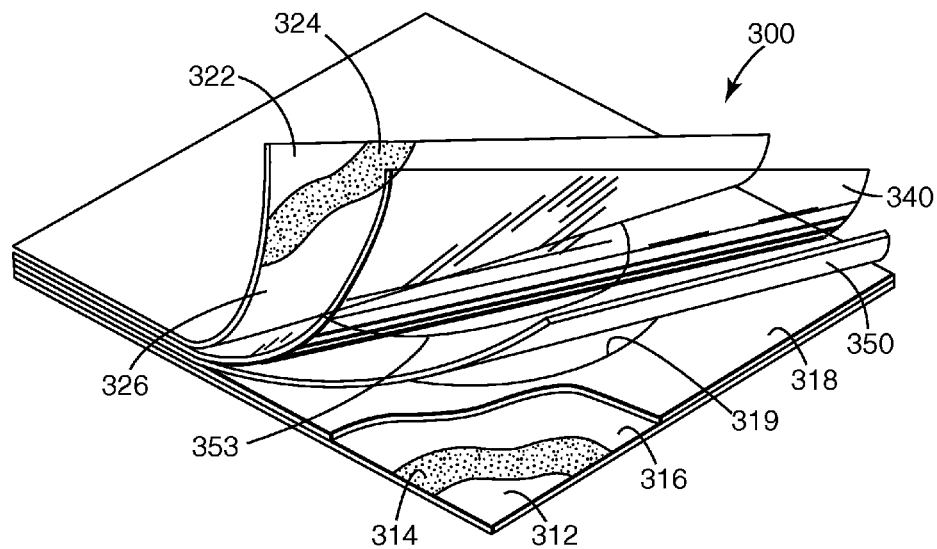

FIG. 3c shows a top perspective view of the article 300 of FIG. 3a. The article 300 comprises a base member 310 that includes a first substrate 112, optional first adhesive layer 114, first dry coating 316 and spacer 318. Also shown in FIG. 3c are the microporous membrane 350, the barrier layer 340, and the cover sheet 320 that includes a second substrate 322, an optional second adhesive layer 324, and a second dry coating 326.

Figure 4:
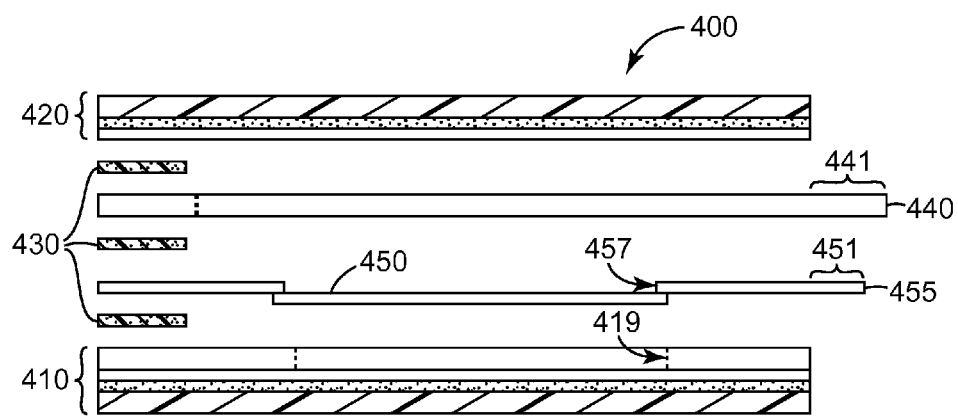
FIG. 4 is an exploded side view of one embodiment of a detection article comprising a spacer and a microporous membrane coupled to a membrane carrier according to the present disclosure.

FIG. 4 shows an exploded side view of another embodiment of a detection article 400 according to the present disclosure. The article 400 comprises a barrier layer 440, a cover sheet 420, and a membrane carrier 455 supporting a microporous membrane 450, all as described herein. The article further comprises a base member 410 that includes a spacer 418 with an aperture 419, as described herein.

The microporous membrane 450 can be configured in the article 400 such that the area of the microporous membrane 450 is coextensive with the aperture 419. In some embodiments, the area of the microporous membrane 450 may be smaller than the area of the aperture 419. In some embodiments, the area of the microporous membrane 450 may be smaller than the area of the aperture 419.

The microporous membrane 450 should be positioned such that, during use, at least of portion of the microporous membrane 450 overlays the aperture 419. Preferably, during use, the microporous membrane 450 is positioned such that the microporous membrane 450 substantially overlays the aperture 419. In some embodiments, the area of the microporous membrane 450 is larger than the area of the aperture 419 and the microporous membrane 450 extends beyond the perimeter of the aperture 419.

Figure 5:
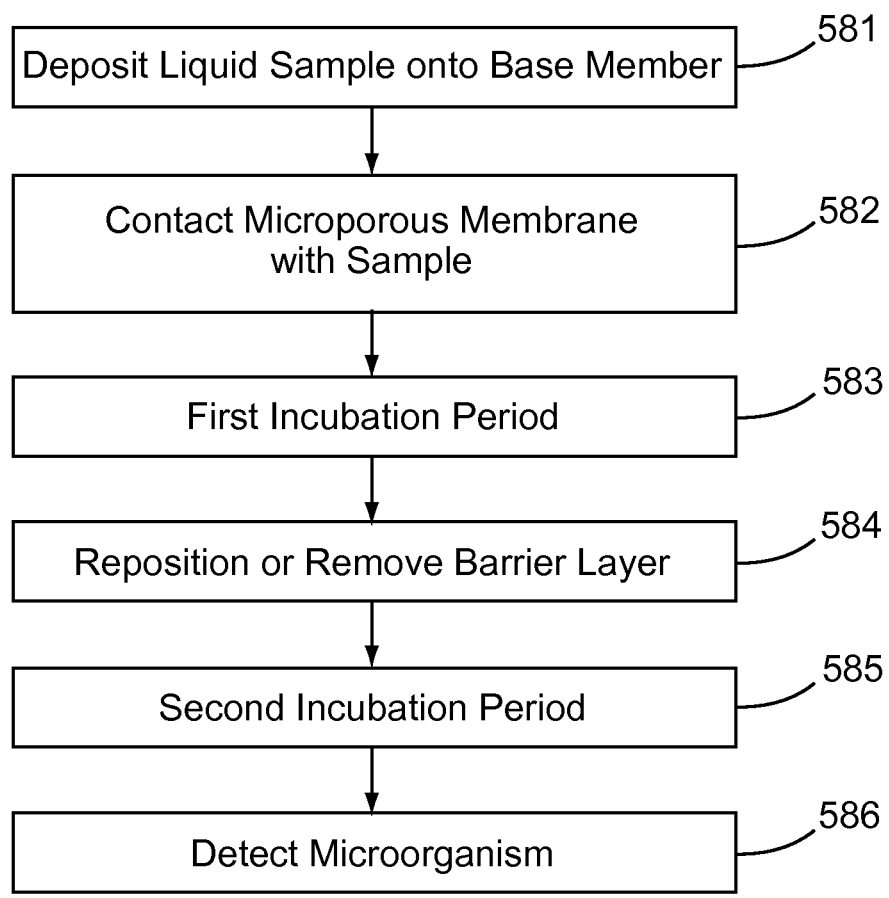
FIG. 5 is a block diagram of one embodiment of a method to detect a microorganism in a liquid sample according to the present disclosure.

Method of Detecting a Microorganism:

The present disclosure provides a method to detect a microorganism in a liquid sample. The method comprises providing a liquid sample suspected of containing a microorganism and any embodiment of a detection article described herein. The article comprises a base member comprising a first dry coating that includes a cold water-soluble gelling agent, a microporous membrane, a cover sheet comprising a second dry coating that includes a detection reagent, and a removable barrier layer that forms a fluid barrier between the microporous membrane and the cover sheet. The microporous membrane is disposed between the base member and the barrier layer. Further steps of the method are shown in FIG. 5.

Optionally, the liquid sample may be mixed or diluted with a nutrient to facilitate the growth of a microorganism (not shown). Optionally, the liquid sample may be mixed or diluted with a selective agent or a detection reagent (not shown). In some embodiments, the liquid sample may be mixed or diluted with any combination of nutrient, a selective agent, and a detection reagent. In some embodiments, the nutrient, selective agent, and/or detection reagent can be added to the liquid sample when the detection article does not comprise a nutrient, selective agent, and/or detection reagent. In some embodiments, the nutrient, selective agent, and/or detection reagent can be added to the liquid sample even though the detection article comprises a nutrient, selective agent, and/or detection reagent.

The method further comprises the process 581 of contacting a predetermined amount of the liquid sample with the base member. Initially, the first dry coating of the base member is exposed. This can be accomplished, for example, by placing an article (see, for example, article 100 of FIGS. 1a and 1c) onto a relatively level surface and lifting the microporous membrane to expose the first dry coating. The microporous membrane can be grasped by the tab region, if present.

After lifting the microporous membrane to expose the first dry coating, a predetermined volume (e.g., 1 mL, 2 mL, 3 mL, 5 mL) of liquid sample is transferred (e.g., poured or pipetted) onto the first dry coating, thereby contacting the first dry coating. In some embodiments, the liquid sample can be deposited into a sample-receiving well formed by the aperture in a spacer that is coupled to the base member comprising the first dry coating.

The method further comprises the process 582 of contacting the microporous membrane with the sample. Contacting the microporous membrane with the liquid sample causes at least a portion of the liquid sample to migrate into the microporous membrane, forming a hydrated region. Contacting the microporous membrane with the liquid sample can be accomplished, for example, simply by lowering the microporous membrane that was lifted to expose the dry coating. The process 582 optionally may further comprise using an inoculum spreading device (e.g., a spreader used to inoculate PETRIFILM plates; available from 3M Company, St. Paul, Minn.) to distribute the liquid sample across a selected portion (e.g., a pre-measured area) of the first dry coating and the microporous membrane.

The method further comprises the process 583 of incubating the article for a first period of time. The first incubation provides the conditions (i.e., time, temperature) to facilitate the growth of a microorganism. A person of ordinary skill in the relevant art will recognize that the incubation temperature may be selected according to the microorganism to be detected. For example, if a yeast or mold is to be detected, the first incubation temperature typically may be from about room temperature (ca. 23° C.) to about 32° C. For example, if a bacterium is to be detected, the first incubation temperature typically may be from about room temperature to about 45° C.

According to the present disclosure, the first incubation period may be as short as about one hour. In some embodiments, the first incubation is less than about 4 hours (e.g., less than about 2 hours, less than about 3 hours, or less than about 4 hours. In some embodiments, the first incubation period is less than about 8 hours (e.g., less than about 5 hours, less than about 6 hours, less than about 7 hours, or less than about 8 hours). In some embodiments, the first incubation is less than about 12 hours (e.g., about 9 hours, about 10 hours, about 11 hours, or about 12 hours. In some embodiments, the first incubation period is less than or equal to about 15 hours (e.g., less than about 13 hours, less than about 14 hours, or less than about 15 hours. In some embodiments, the first incubation period is up to 48 hours (e.g., less than about 24 hours, less than about 36 hours, or less than about 48 hours.

The method further comprises the process 584 of repositioning the barrier layer. The barrier layer is repositioned to provide contact between at least a portion of the hydrated region of microporous membrane and at least a portion of the second dry coating. Preferably, the barrier layer is repositioned to provide contact between the entire hydrated region of the microporous membrane and the second dry coating. The barrier layer may be repositioned, for example, by twisting or folding the barrier layer to provide contact between the hydrated region and the second dry coating. In a preferred embodiment, the barrier layer can be removed from the detection article (i.e., the barrier layer is loosely inserted in the article or is detachably attached to the article) to provide contact between the hydrated region of the microporous membrane and the second dry coating.

Contact between the hydrated region of the microporous membrane and the second dry coating permits hydration of the second dry coating and, thereby, the interaction of an detection reagent, lysis agent, or selective agent in the second dry coating with a microorganism, a component of a microorganism, and/or a metabolic byproduct of a microorganism. The interaction can provide a detectable signal.

The method further comprises the process 585 of incubating the article for a second period of time. In some embodiments, the incubation temperature for the second period of time can be the same temperature that was used for the first period of time. In some embodiments, the incubation temperature for the second period of time can be different than the temperature that was used for the first period of time. Advantageously, the incubation temperature for the second period of time can be higher than the temperature that was used for the first period of time, thereby reducing the time needed to observe a detectable signal.

According to the present disclosure, the second incubation period should be an amount of time sufficient to observe a detectable signal. In some embodiments, the second incubation period preferably is a shorter period than the first incubation period. In combination with any of the above first incubation periods, the second incubation period may be as short as about 15 minutes. In combination with any of the above first incubation periods, the second incubation is less than about 30 minutes. In combination with any of the above first incubation periods, the second incubation period is less than or equal to 4 hours (e.g., less than or equal to about 1 hour, less than or equal to about 2 hours, less than or equal to about 3 hours, or less than or equal to about 4 hours). In combination with any of the above first incubation periods, the second incubation is less than or equal to 8 hours (e.g., less than or equal to about 5 hours, less than or equal to about 6 hours, less than or equal to about 7 hours, or less than or equal to about 8 hours). In combination with any of the above first incubation periods, the second incubation period is less than or equal to 12 hours (e.g., less than or equal to about 9 hours, less than or equal to about 10 hours, less than or equal to about 11 hours, or less than or equal to about 12 hours). combination with any of the above first incubation periods, the second incubation period is up to about 96 hours (e.g., less than or equal to about 48 hours, less than or equal to 72 hours, less than or equal to about 96 hours.

The method further comprises the process 586 of observing an indication of the presence or absence of microbial growth. The indication may be observable visually and/or by an instrument (e.g., an imaging system) and both types (manual and automated) of detection are contemplated by the present disclosure.

The nature of the indication of microbial growth generally is dependent upon the detection reagent (or plurality of detection reagents) in the article. For example, certain detection reagents (e.g. enzyme substrates) produce a detectable colored or fluorescent product when they interact with a microbe or a component thereof. For example, certain detection reagents (e.g., pH indicators) produce a detectable change in color or fluorescence in the presence of acidic or basic metabolic products of microorganisms. For example, certain detection reagents (e.g., polysaccharide or polypeptide polymers) are relatively opaque in their native state and become relatively transparent when degraded by microorganisms or components thereof.

In some embodiments, an indication of the presence of microbial growth comprises the presence of a detectable microbial colony. The microbial colony may be detected visually. The microbial colony may be detected using an imaging system. Suitable systems for detecting microbial colonies are described, for example, in International Patent Publication No. WO 2005/024047; U.S. Patent Application Publication Nos. US 2004/0101954 and US 2004/0102903; and U.S. Patent Application No. 61/187,107 filed on Jun. 15, 2009; each of which is incorporated herein by reference in its entirety. Non-limiting examples of suitable imaging systems include PETRIFILM Plate Reader (PPR), available from 3M Company (St. Paul, Minn.), the PETRISCAN Colony Counter available from Spiral Biotech (Norwood, Mass.), and PROTOCOL and ACOLYTE plate scanners available from Synbiosis (Cambridge, U.K.)

In some embodiments, an indication of the presence of microbial growth comprises the presence of a reaction, detected visually or by instrument, associated with a non-visually-detectable microbial colony.

In any one of the above embodiments, the method can further comprise enumerating microorganisms. In some embodiments, the microorganisms can be enumerated by counting the number of discrete colonies in the article. In some embodiments, the microorganisms can be enumerated by counting the number of discrete reactions (e.g., colored zones, fluorescent zones, clear zones) that are associated with non-visually-detectable colonies in the article. Enumerating microorganisms may comprise using an imaging system to enumerate microorganisms.

Observing an indication of the presence or absence of microbial growth may comprise obtaining an image of the article. Observing an indication of the presence or absence of microbial growth may further comprise printing, displaying, or analyzing the image.

The invention will be further illustrated by reference to the following non-limiting Examples. All parts and percentages are expressed as parts by weight unless otherwise indicated.

EXAMPLES

All parts, percentages, ratios, etc. in the examples are by weight, unless noted otherwise. Solvents and other reagents used were obtained from Sigma-Aldrich Chemical Company; Milwaukee, Wis. unless specified differently.

Example 1

Preparation of Microporous Membrane Carrier:

An annular gasket was die-cut from biaxially-oriented polypropylene (BOPP, 1.6 mil (0.04 mm) thickness) film coated with a thin layer of water-insoluble adhesive (96 wt. % iso-octyl acrylate and 4 wt. % acrylic acid). The outer diameter of the gasket was approximately 52.5 mm and the inner diameter of the gasket was approximately 45 mm.

A circular hole (approximately 44 mm diameter) was die cut from a rectangular sheet (approximately 75 mm by 95 mm) of BOPP (0.04 mm thickness). A nylon membrane filter (47 mm, 0.45 mm nominal pore size, obtained from Alltech Associates (Deerfield, Ill.) was centered over the hole on the adhesive-coated side of the BOPP sheet. The adhesive side of the gasket was centered over the outer edge of the membrane filter and was pressed against the filter and the BOPP sheet, sealing the edge of the membrane filter to the BOPP sheet.

Preparation of Detection Article:

A base member was prepared as follows. A plastic film (Microamp Optical Adhesive Film, part number 4311971 from Applied Biosystems, Foster City, Calif.) comprising silicone adhesive on one major surface was powder coated (on the adhesive surface) was powder coated with a combination of Meyprogat Guar (M150) and Standard Methods Nutrients Broth at a ratio of 2:1, as described in U.S. Pat. No. 4,565,783. The composition of the Standard Methods Nutrients Broth is listed in Table 1. The coating weight of the powder was approximately 8 grains per 24 square inches. A foam spacer (polystyrene capliner foam, 0.5 mm thick, American Fuji Seal Inc., Bardstown, Ky.) with a thin layer of water-insoluble adhesive on one side and a circular aperture of about 5 cm was laminated to the coated side of the base member.

TABLE 1

Standard Methods Nutrients Broth Formulation.
All components were added as powders and thoroughly mixed before use.

| Component | Weight Percent |
| --- | --- |
| Pancreatic digest of casein | 22.7 |
| Yeast extract | 15.9 |
| Sodium pyruvate | 45.5 |
| Dextrose | 4.1 |
| Potassium phosphate, dibasic | 9.0 |
| Potassium phosphate, monobasic | 2.8 |
| Sodium carbonate | A small amount of sodium carbonate was added such that, when dissolved in |

TABLE 1-continued

Standard Methods Nutrients Broth Formulation.
All components were added as powders and thoroughly mixed before use.

| Component | Weight Percent |
|---|---|
| | deionized water, the mixture had a pH approximately 7.0. |

A cover sheet was prepared. Microamp Optical Adhesive Film with a thin layer of transfer adhesive was powder coated with a mixture of Standard Methods Nutrients broth and 0.2% wt/wt Triphenyl Tetrazolium Chloride. The coating weight of this mixture was approximately 8 grains per 24 square inches.

A multilayer detection article was prepared as follows. The base member was placed on a level surface with the coated side facing up. The microporous membrane carrier was placed onto the base member with the gasket side facing away from the base member. The membrane was centered over the circular aperture in the spacer of the nutrient film. A barrier layer of BOPP (approximately 75 mm by 95 mm by 0.4 mm thick) was placed over the membrane layer. The cover sheet was placed over the barrier layer with the coated side of the cover sheet facing the barrier layer. The four-layer stack of films was then stapled along one side.

Example 2

A detection article was made as in Example 1, with the exception that the membrane carrier was made from a BOPP film that did not include a thin layer of adhesive on one side.

Example 3

The detection article was inoculated with *Staphylococcus aureus* ATCC 6538 (1 mL of 100 CFU/mL solution) and incubated at 37 C for 6 hours. The barrier film was then removed and incubation continued at 37 C until 24 hours after inoculation. Individual red colonies were visible through the base member. A reddish area of growth was also visible through the cover sheet, although the colonies were not as sharply defined as when viewed through the base member. Wetting of the microporous membrane by the liquid sample was observed. The colonies were photographed with a digital camera.

Example 4

The detection articles of Example 2 was inoculated with 100 colony forming units of *Staphylococcus aureus* (ATCC 6538) and incubated at 37 C. After 6 hours and 8 hours of incubation, respectively, individual articles were removed from the incubator and the barrier film was removed. After removal of the barrier films, the articles were incubated at 37 C until 24 hours after inoculation. Red colonies were observed in the articles.

Example 5

The detection articles of Example 1 inoculated with 100 colony forming units (CFU) of *Pseudomonas aeruginosa* (ATCC 9027) and incubated at 37 C for 6 to 8 hours, respectively. The barrier film was removed and incubation continued at 37 C until 24 hours after inoculation. Red colonies were observed in the articles.

Examples 6-7 and Comparative Examples C-1 and C-2

A detection article was constructed as in Example 2 and was inoculated with *Pseudomonas fragi* (ATCC 51821) at a concentration of about 100 colony forming units (Example 6). A second detection article was constructed as in Example 2 and was inoculated with *Microbacterium* esteraromaticum (ATCC 51822) at a concentration of about 100 colony forming units (Example 7). For comparison, 3M PETRIFILM Aerobic Count plates (available from 3M Company, St. Paul, Minn.) were also inoculated with *Pseudomonas fragi* and *Microbacterium* esteraromaticum (Comparative Examples C-1 and C-2, respectively) at a concentration of about 100 colony forming units for each plate.

The samples were incubated at 28 C for 6 hours. The barrier films were then removed from Examples 6 and 7 and incubation continued at 28 C. Twenty hours after inoculation, colonies were faintly visible for Examples 6 and 7, but not for Comparative Examples C-1 and C-2. Twenty-four hours after inoculation, colonies were clearly visible for Examples 6 and 7, but colonies were not visible for Comparative Examples C-1 and C-2. Forty-eight hours after inoculation, colonies were visible for Comparative Examples C-1 and C-2. These examples show that allowing growth to occur for a period of time before the cells are exposed to a detection reagent (TTC) can result in a shorter time to detection.

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

What is claimed is:

1. A method of detecting the presence or absence of a microorganism in a sample, comprising:
   providing,
     a liquid sample suspected of containing a microorganism;
     a detection article comprising:
       a base member comprising a first dry coating that includes a cold water-soluble gelling agent;
       a microporous membrane;
       a cover sheet comprising a second dry coating that includes a first detection reagent;
       a barrier layer that forms a fluid barrier between the microporous membrane and the cover sheet;
       wherein the microporous membrane is disposed between the base member and the barrier layer;
   contacting a predetermined amount of the sample with the first dry coating;
   contacting the microporous membrane with the sample;
   incubating the article for a first period of time;
   repositioning the barrier layer to provide contact between the cover sheet and the microporous membrane;
   incubating the article for a second period of time; and
   observing an indication of the presence or absence of microbial growth.

2. The method according to claim 1, wherein repositioning the barrier layer comprises removing the barrier layer from the article.

3. The method according to claim 1, wherein the article further comprises a spacer that forms a sample-receiving well with the base member, wherein contacting a predetermined amount of the sample with the first dry coating comprises transferring the sample into the sample-receiving well.

4. The method according to claim 1, further comprising mixing the sample with a nutrient, a selective agent, a second detection reagent, or a combination of any two or more of the foregoing.

5. The method according to claim 1, wherein the first period of time is about 1 hour to about 48 hours.

6. The method according to claim 5, wherein the first period of time is about 4 hours to about 6 hours.

7. The method according to claim 1, wherein the second period of time is about 15 minutes to 96 hours or less.

8. The method according to claim 7, wherein the second period of time is about 15 minutes to about 6 hours.

9. The method according to claim 7, wherein the second period of time is about 2 hours to about 4 hours.

10. The method according to claim 1, wherein at least a portion of the first dry coating comprises a plurality of detection reagents, wherein observing an indication of microbial growth comprises detecting and differentiating two or more types of microorganisms.

11. The method according to claim 1, wherein observing an indication of the presence or absence of microbial growth comprises enumerating at least one type of microorganism.

12. The method according to claim 1, wherein observing an indication of the presence or absence of microbial growth comprises obtaining an image of the article.

13. The method according to claim 12, wherein observing an indication of the presence or absence of microbial growth further comprises printing, displaying, or analyzing the image.

* * * * *